Figure 1C:
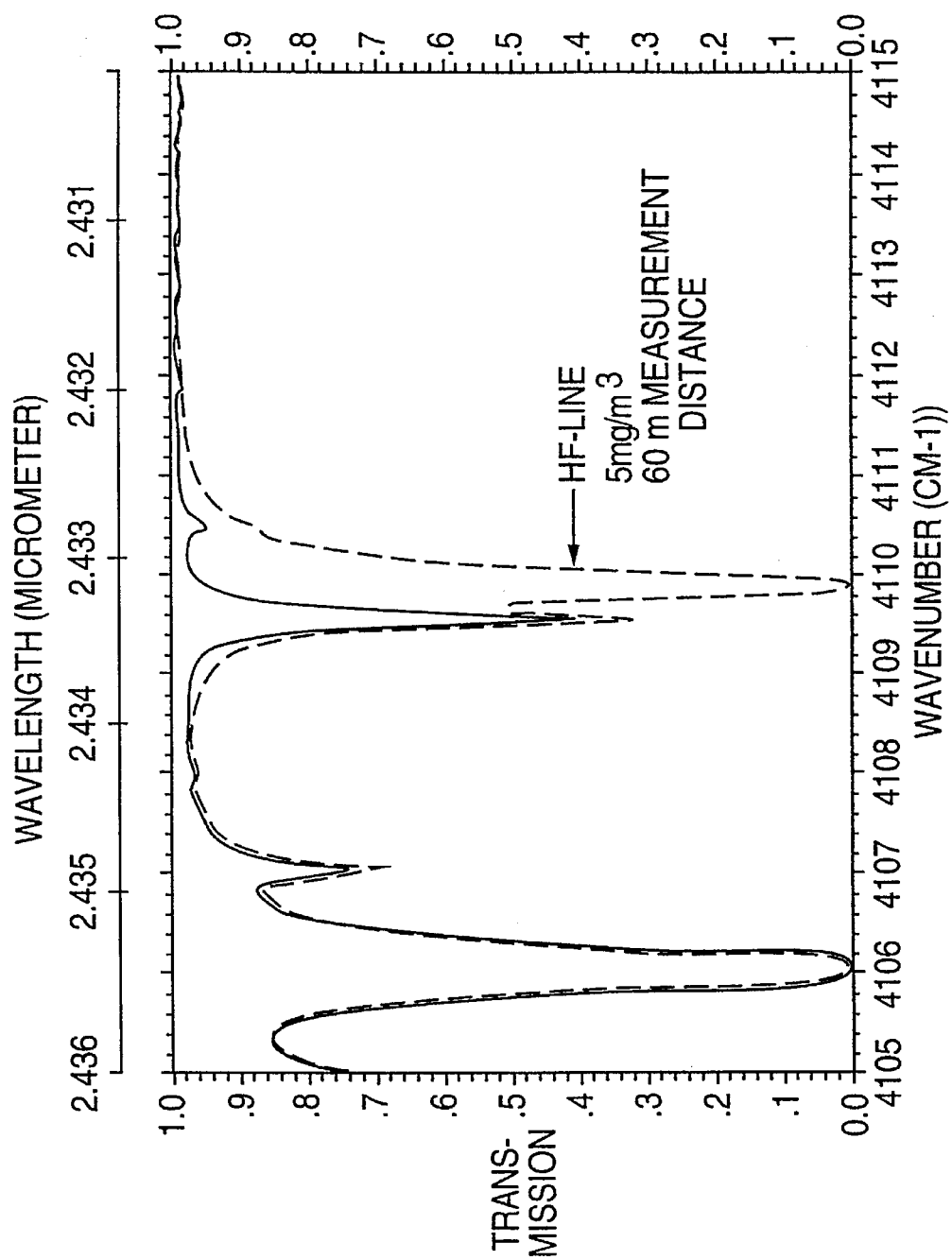

United States Patent
Foosnæs et al.

[11] Patent Number: 5,606,419
[45] Date of Patent: Feb. 25, 1997

[54] SPECTROSCOPIC MEASURING DEVICE HAVING FILTER CONSISTING OF INTERFERENCE FILTER, ONE OR TWO FIXED-MIRROR ETALONS AND A SINGLE MOVABLE-MIRROR ETALON

[75] Inventors: Trygve Foosnæs, Ardalstangen; Tycho Jæger, Skedsmokorset; Jon Tschudi, Oslo; Jon K. Hagene, Dilling, all of Norway

[73] Assignee: Norsk Hydro a.s., Oslo, Norway

[21] Appl. No.: 433,409

[22] PCT Filed: Nov. 18, 1993

[86] PCT No.: PCT/NO93/00170

§ 371 Date: Aug. 3, 1995

§ 102(e) Date: Aug. 3, 1995

[87] PCT Pub. No.: WO94/11713

PCT Pub. Date: May 26, 1994

[30] Foreign Application Priority Data

Nov. 18, 1992 [NO] Norway .................................. 924443

[51] Int. Cl.$^6$ ................ G01J 3/51; G01N 21/61
[52] U.S. Cl. .......................... 356/419; 356/346
[58] Field of Search .............. 356/346, 416, 356/419

[56] References Cited

U.S. PATENT DOCUMENTS

| 3,373,651 | 3/1968 | Mack et al. | 356/346 |
| 3,914,055 | 10/1975 | Wolga et al. | 356/346 |
| 4,035,643 | 7/1977 | Barrett | 356/346 X |
| 4,525,067 | 6/1985 | Hernandez | 356/346 |

FOREIGN PATENT DOCUMENTS

0543578 5/1983 European Pat. Off. .

Primary Examiner—Vincent P. McGraw
Attorney, Agent, or Firm—Wenderoth, Lind & Ponack

[57] ABSTRACT

In the present equipment for spectroscopic measurement of a gas in a gas mixture, for example a gas in the atmosphere, a filter device is used to filter out one spectral line from other spectral lines belonging to other gases and the transmitted light is detected by a detector which gives a signal to devices for calculating and displaying the measurement data. The filter device consists of an interference filter (1), at least one fixed etalon (2) and a Fabry-Perot interferometer (1). In a preferred design, the filter can be fitted with two fixed etalons instead of one.

4 Claims, 8 Drawing Sheets

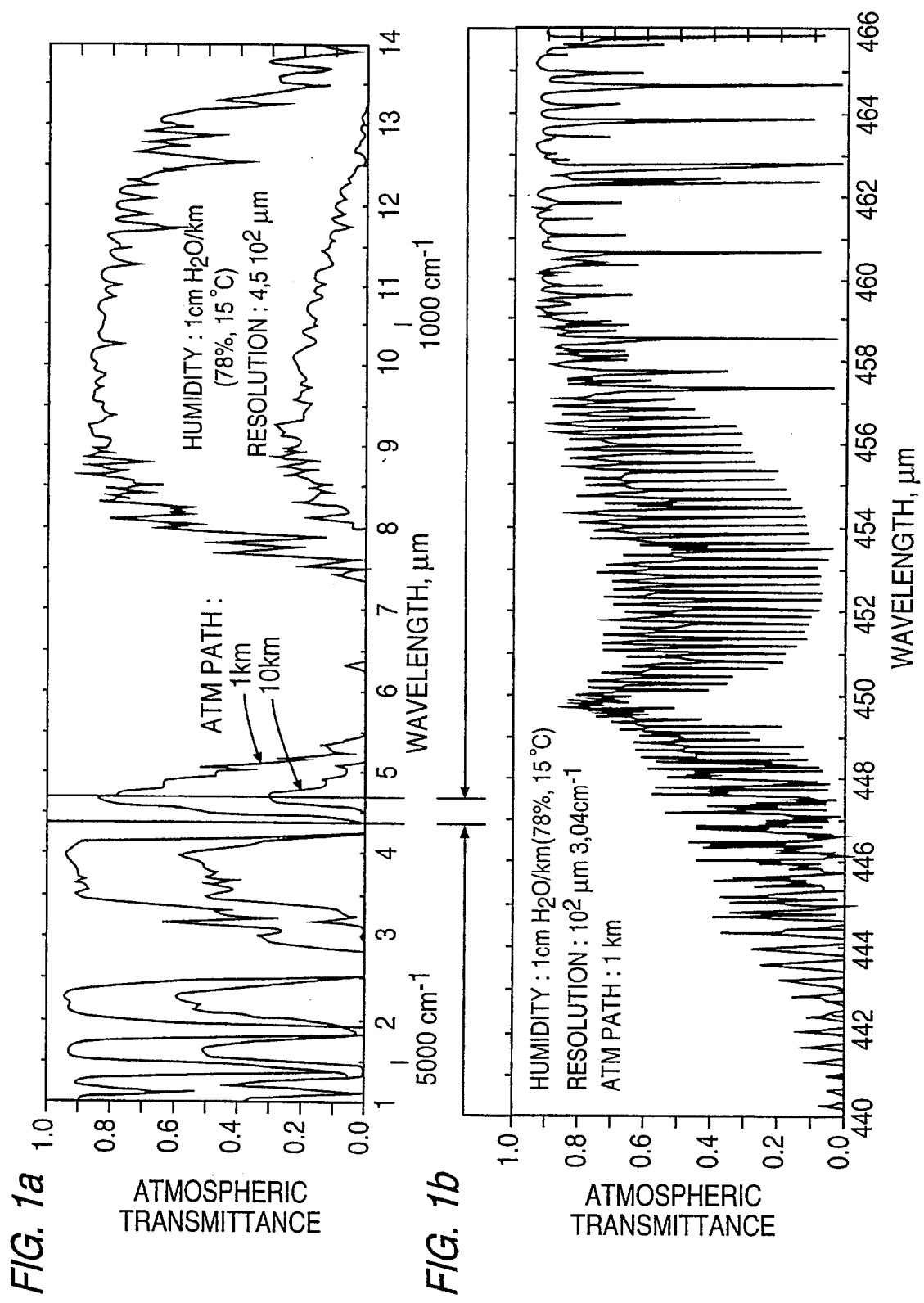

SPECTROSCOPIC MEASURING DEVICE HAVING FILTER CONSISTING OF INTERFERENCE FILTER, ONE OR TWO FIXED-MIRROR ETALONS AND A SINGLE MOVABLE-MIRROR ETALON

The present invention concerns equipment for the spectroscopic measurement of a gas in a gas mixture, in which a filter device is used to filter out one spectral line from other spectral lines belonging to other gases and in which the transmitted light is detected by a detector which sends a signal to devices for calculating and displaying the measurement data.

Gas measurement instruments based on spectroscopic methods are available for a number of different gases and are more or less advanced/complicated. The simplest instruments use optical interference filters which select a certain spectral range in which the gas in question absorbs. For reasons of production technology the filters are relatively wide and there is a high probability that several gases will have adsorption lines within the filter's transmission band. Such instruments can therefore not be made particularly sensitive unless there is certainty that all interfering gases have been removed in advance. The greatest problem in this connection is often water vapour which has numerous adsorption lines over a broad spectrum. When used in industrial circumstances it is necessary for the gas samples to be dried before measurement can take place and this makes continuous monitoring of discharges impossible in practice.

At the other end of the scale there are so-called Fourier Transform Instruments (FTS) which are designed to measure a number of gases and which, for this reason, cover a broad spectrum. The instruments usually have a built-in "library" with spectra which are used for identifying individual elements. The instruments are very expensive and are in practice not very well suited for practical industrial applications.

The equipment of the present invention has been designed for spectroscopic measurement of a gas and represents a practical solution which is exceptionally well suited for industrial applications and which is considerably simpler in its design and less expensive than the existing solutions.

The present invention is characterised in that the filter device consists of an interference filter, at least one fixed etalon and a Fabry-Perot interferometer.

With the solution defined here it is possible to realise a spectral resolution of approximately $0.1 \text{ cm}^{-1}$ which is necessary to achieve a measurement over a single absorption line.

Figure 2:
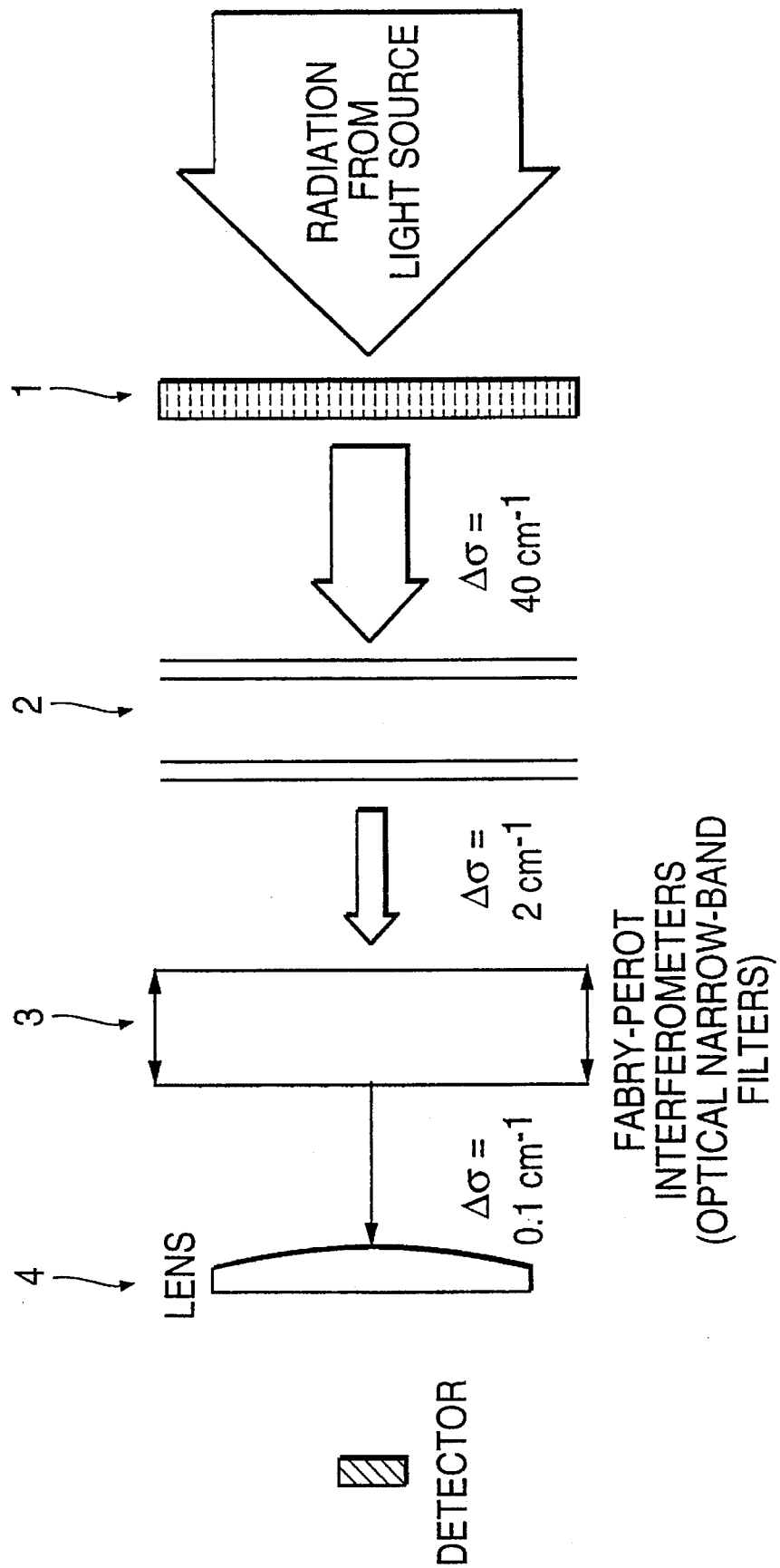

The present invention will now be described in more detail by means of examples and with reference to the attached drawings, of which FIG. 1 shows a spectrum of the atmosphere, FIG. 2 shows the basic optical elements of the equipment in accordance with the present invention, and FIGS. 3–7 show how the transmission takes place between the components shown in FIG. 2.

Development of the equipment in accordance with the present invention was based on in situ measurement in real time of the gas concentration of hydrogen fluoride (HF). In situ here means that the measurement and the measuring equipment are placed where it is relevant to determine the gas concentration of HF, for example in the atmosphere, and real time means that the measuring result exists after an interval of time which is shorter than the time resolution with which the measurement results are to be described.

Even though the equipment as described was developed to measure HF, we would here like to note, that with only a few modifications it can be used for measuring other gases.

All gases can be characterised by their specific absorption spectra. In practice this means that visible light and thermal radiation (infrared radiation) are absorbed at very specific frequencies or wavelengths. In other words, these characteristic frequencies characterise each individual gas. The reason for these characteristic adsorptions is linked with the fact that gas molecules carry out complex "mechanical" oscillations. The molecules can vibrate and rotate and, therefore, these adsorption spectra are usually called vibration-rotation spectra. The complexity of these spectra is very different for different gases. Carbon dioxide, for example, has many thousands of characteristic adsorption lines in the frequency range which is of practical interest, whereas hydrogen fluoride only has in the order of 100 lines. FIG. 1 shows a spectrum of the atmosphere. The transmittance or translucence is measured over the whole frequency range which is of significance for remote measurement, i.e. the spectral range 1–14 µm. FIG. 1a shows the entire absorption spectrum for a normal atmosphere with no particular pollution, but with a low spectral resolution. FIG. 1b shows a small segment of the spectrum with a high spectral resolution. All the lines in this spectrum can be ascribed to one of the gases in the atmosphere. Most strong lines and adsorption bands stem from water vapour. In the spectral range from 4.40–4.66 µm there are mainly spectral lines for $CO_2$, CO, $NO_x$ and $H_2O$ in a "normal" atmosphere. If a foreign gas is added to a "normal atmosphere", for example HF gas, this will be shown directly in the form of the spectrum and a number of new adsorption lines will appear which are specific for this gas. By selecting a single adsorption line for HF (or another gas which is to be measured) for which it has been proven that any other gases do not adsorb, the gas concentration for HF can be measured by measuring the adsorption for this adsorption line. FIG. 1c shows a dotted line for a calculated spectrum for an atmosphere with 5 mg HF/m³ and, for comparison, a spectrum for an atmosphere without HF is shown as an unbroken line. The concentration of HF can, as stated, be determined from the form of such an HF line, a technique which is called "single-line spectroscopy".

On the basis of the experience gained from using FTS instruments, we saw the possibility of developing simple, cheap, in situ equipment based on "single-line spectroscopy" and succeeded in our aim by producing a solution with such equipment as is shown in more detail in FIG. 2.

More precisely, the figure shows the basic optical elements of the equipment or sensor for measuring HF. The components comprise an optical interference filter 1, two fixed etalons 2, an etalon with movable mirrors (Fabry-Perot interferometer) 3, a lens 4, and a detector 5. The light arrives from a light source (not shown in detail) after having passed through the gas which is to be measured and being transmitted first through the optical interference filter 1 where the wavenumber range Δw "is limited" to a range corresponding to 40 cm⁻¹. Subsequently, the light is transmitted through the two fixed etalons 2 where the transmission is narrowed further to 2 cm⁻¹ and on to the Fabry-Perot interferometer where the transmission is finally restricted to 0.1 cm⁻¹. The lens which is arranged after the Fabry-Perot interferometer focuses the incident in on the detector.

FIGS. 3–6 show how the transmission takes place through the optical components which are mentioned above. The transmission is shown as a function of the wavenumber of the light. The figures are standardised so that the maximum transmission is set at 1. This means that losses are not included but they will be independent of the wavelength within the range the figures cover.

Figure 3A:
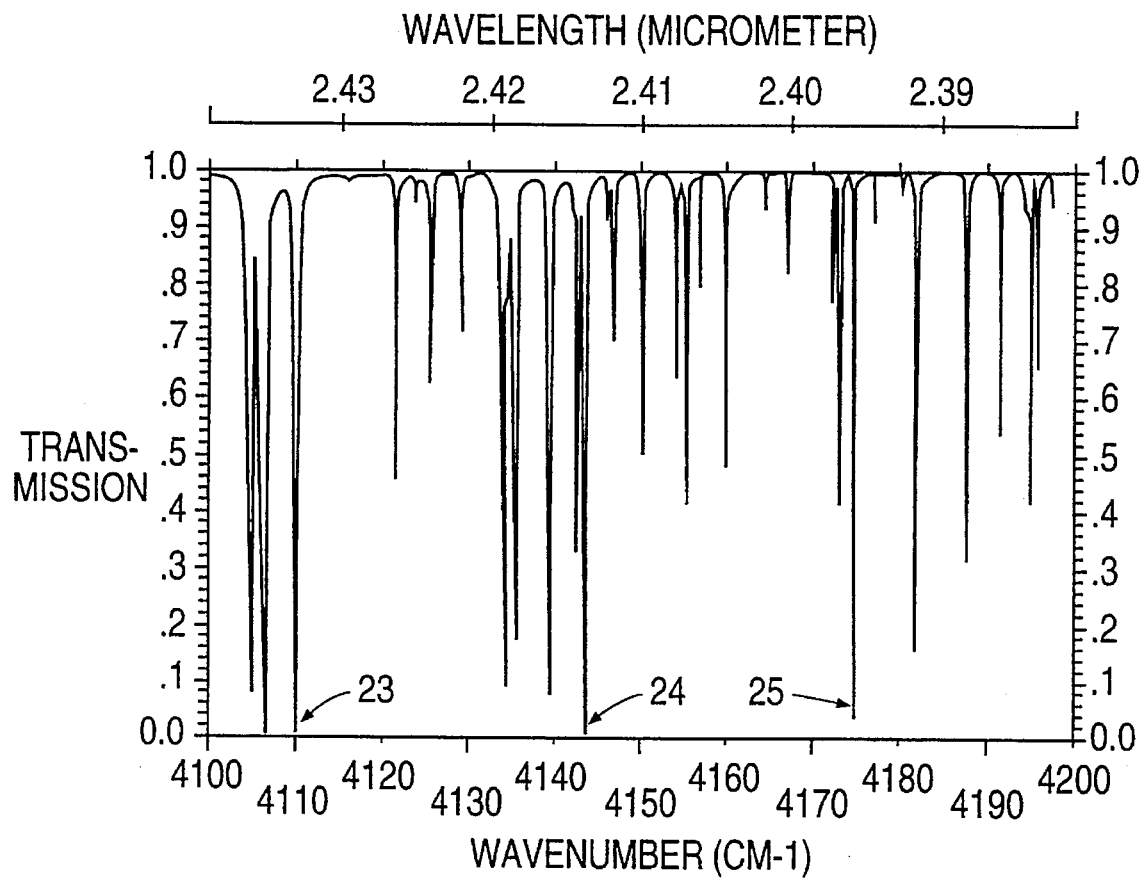
Figure 3B:
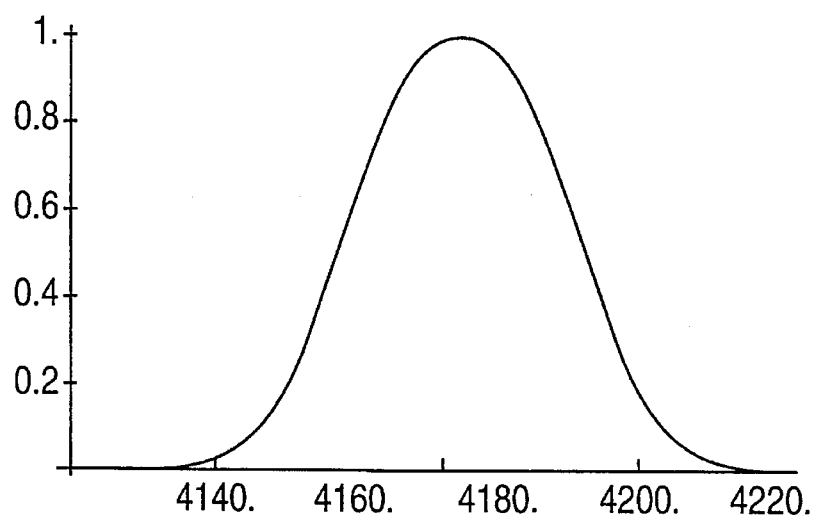

FIG. 3 shows an atmosphere spectrum in which the HF lines R3, R4 and R5 are marked. FIG. 3b shows the transmission through the band-pass filter, where the maximum transmission will coincide with the R5 line which is the best one to use in the HF measuring sensor.

Figure 4A:
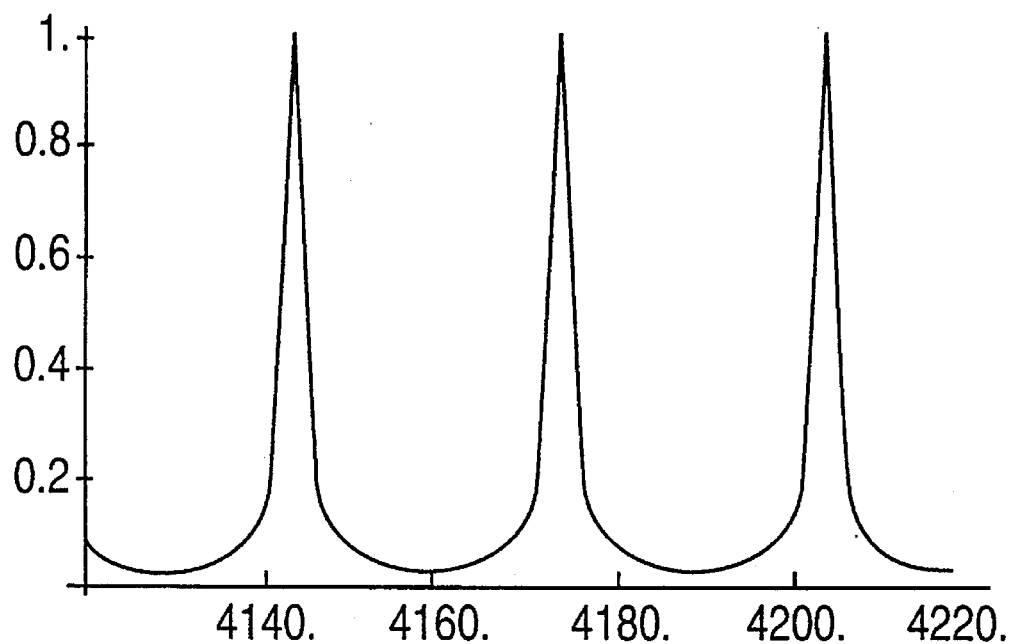
Figure 4B:
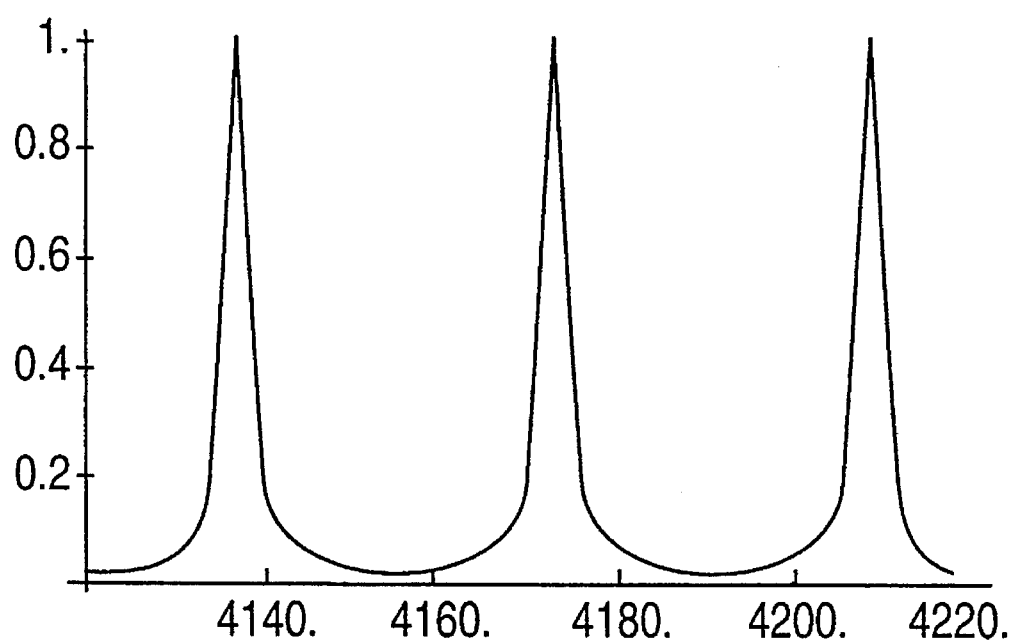

The transmission through each of the two fixed etalons is shown in FIGS. 4a and 4b. Please note that the transmission for each etalon is a periodic function of the wavelength. The distance between the "peaks" and their exact position will depend on the distance between the mirror surfaces in each etalon.

The width of the "peaks" will also depend on the coefficients of reflection of the mirror surfaces.

Figure 5A:
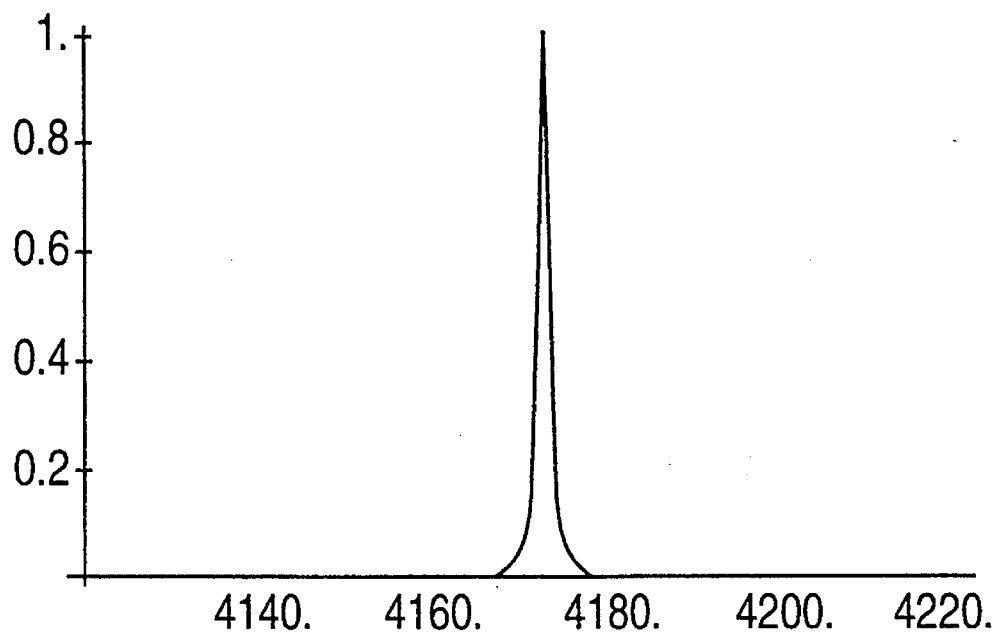
Figure 5B:
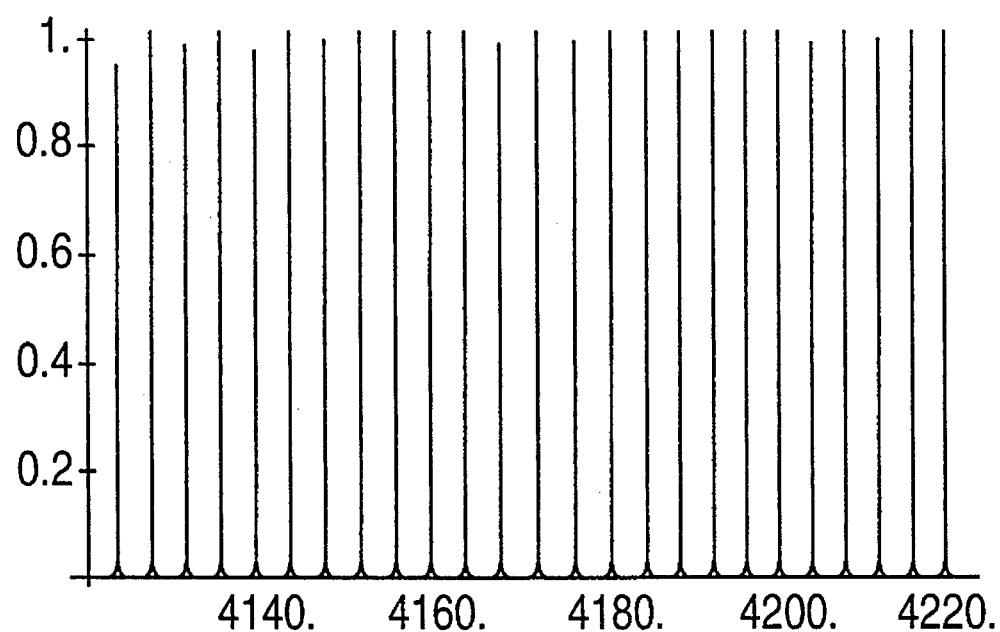

The total transmission through the interference filter and the two fixed etalons is shown in FIG. 5a. FIG. 5b shows the transmission through the etalon with movable mirrors. The interference filter and the two fixed etalons cause only the light with a frequency within the "lobe" which is marked on FIG. 5b to be transmitted to the detector.

Figure 6A:
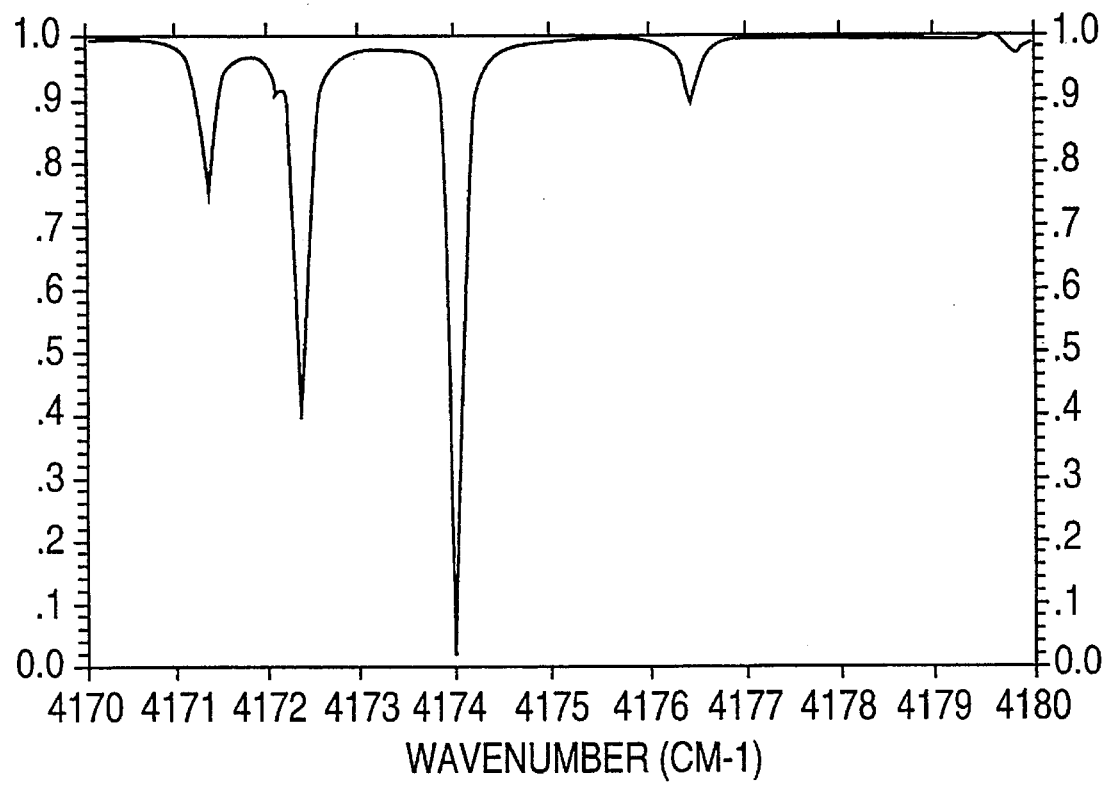
Figure 6B:
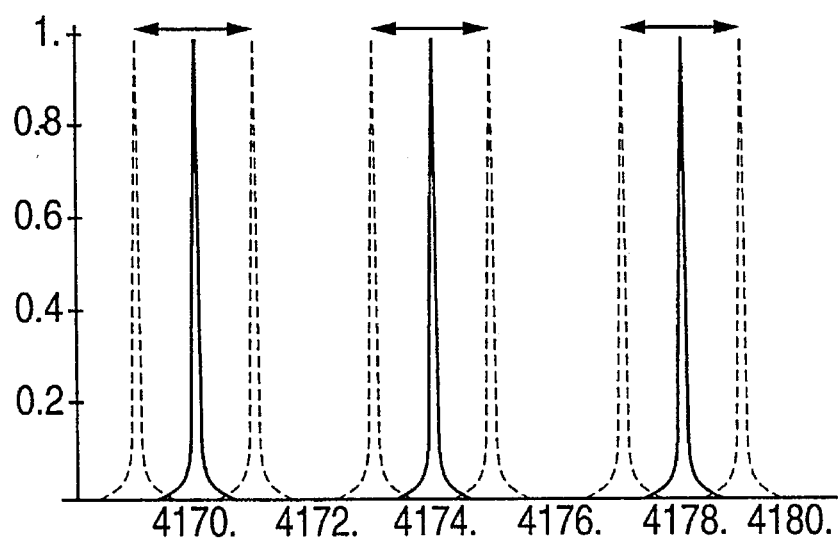

FIG. 6a shows a part of the spectrum enlarged with the HF line R5 marked. A section of FIG. 5b is enlarged in FIG. 6b. The dotted lines show how the transmission curve for this etalon will "move" when the distance between the mirrors is altered. This can be done using piezoelectric translators.

Figure 7A:
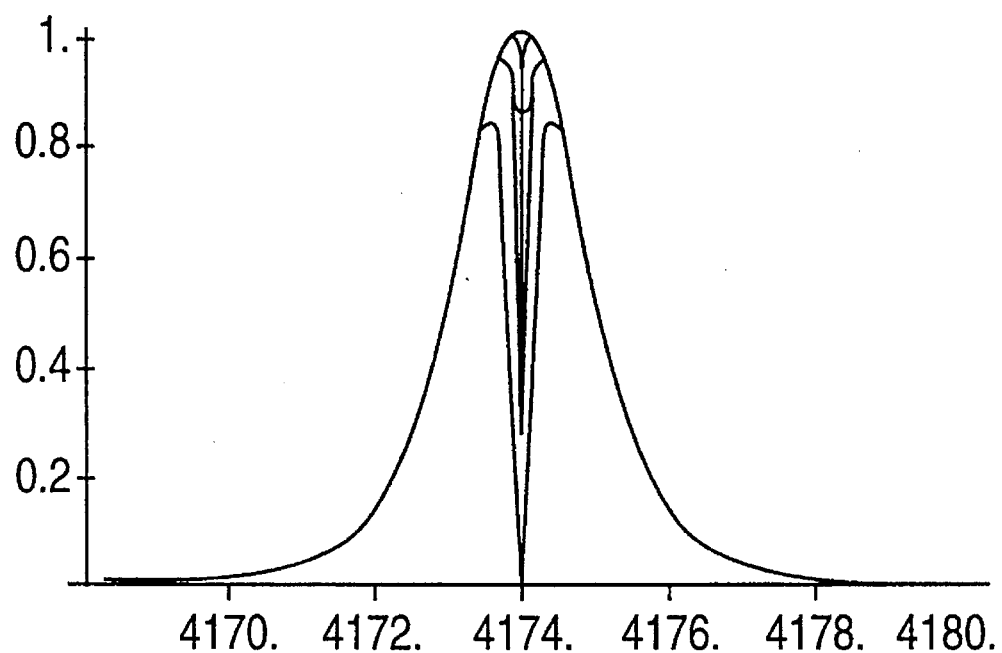
Figure 7B:
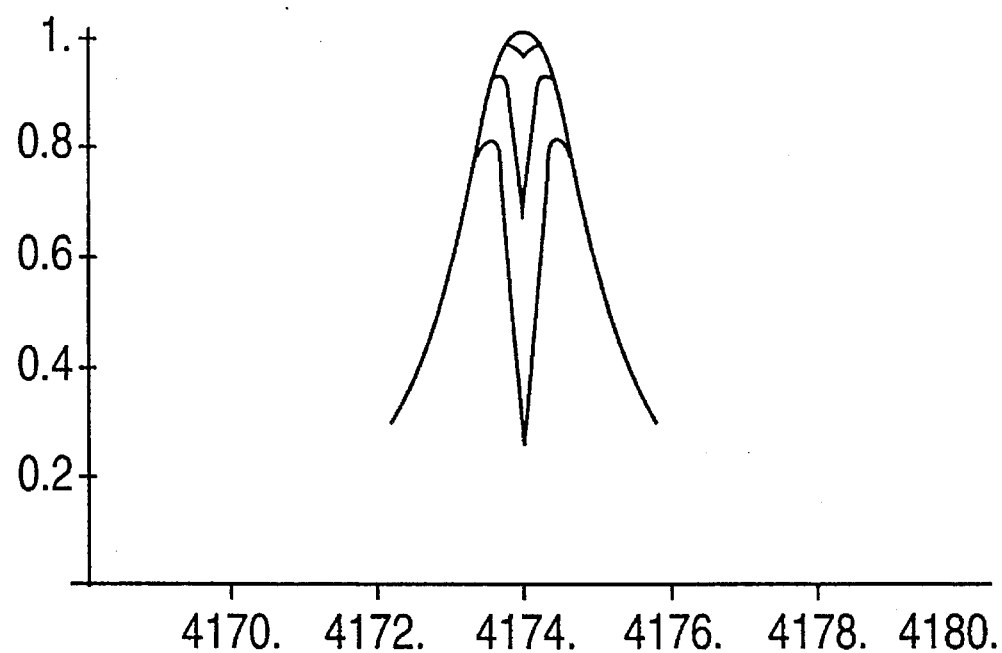

FIG. 7a shows an enlarged section of 4a together with the spectrum for three different concentrations of HF, respectively 0.05 mg/m$^3$, 0.5 mg/m$^3$ and 5 mg/m$^3$ at a 200 m measuring distance after passing through the two fixed etalons and the interference filter. FIG. 7b shows the signal the detector will give when the etalon with movable mirrors "scans" over the spectral line.

Regarding the equipment for handling the signal given off by the detector, please note that the signal is digitalised and transmitted to a microprocessor. This calculates the area below the adsorption line, for example R5 for HF which is the measurement gas in the above-mentioned example, and the concentration of HF is a function of this area. The measurement results may, in turn, be displayed on a graphic screen or plotter.

Please note that the signal-handling equipment, the slides and any "pre-optics" do not represent an essential part of the present invention and that these parts of the equipment are, therefore, not discussed in further detail or shown in FIG. 2 which shows the principal parts of the solution in accordance with the present invention.

Furthermore, please note in particular that the present invention is not restricted to use with two fixed etalons; one fixed etalon may also be used.

However, calculations have shown that the need for an etalon with movable mirrors (Fabry-Perot) is reduced if two fixed etalons are used instead of one. This is because two etalons provide a better spectral contrast, i.e. less transmission of the wavelengths which are not supposed to reach the detector.

We claim:

1. Equipment for the spectroscopic measurement of a gas in a gas mixture, for example a gas in the atmosphere, in which a filter device is used to filter out one spectral line from other spectral lines belonging to other gases and in which the transmitted light is detected by a detector which gives a signal to devices for calculating and displaying the measurement data, characterised in that the filter device consists of an interference filter, at least one fixed etalon having non-movable mirrors spaced apart by a fixed gap and a Fabry-Perot interferometer having movable mirrors spaced apart by an adjustable gap.

2. Equipment in accordance with claim 1, characterised in that said at least one fixed etalon is two fixed etalons each having non-movable mirrors spaced apart by a fixed gap.

3. A radiation filter of a spectroscopic measurement apparatus, said filter for receiving radiation containing spectral information of an atmosphere and filtering out a single spectral line of a gas to be measured within the atmosphere from among spectral lines of other gases within the atmosphere, said filter consisting essentially of an interference filter, a single fixed etalon having non-movable mirrors spaced apart by a fixed gap, and a single Fabry-Perot etalon having movable mirrors spaced apart by an adjustable gap, arranged in succession between a source of the radiation and a detector of the measurement apparatus.

4. A radiation filter of a spectroscopic measurement apparatus, said filter for receiving radiation containing spectral information of an atmosphere and filtering out a single spectral line of a gas to be measured within the atmosphere from among spectral lines of other gases within the atmosphere, said filter consisting essentially of an interference filter, a first fixed etalon having non-movable mirrors spaced apart by a first fixed gap, a second fixed etalon having non-movable mirrors spaced apart by a second fixed gap, and a single Fabry-Perot etalon having movable mirrors spaced apart by an adjustable gap, arranged in succession between a source of the radiation and a detector of the measurement apparatus.

* * * * *